(12) United States Patent
Kreh et al.

(10) Patent No.: US 7,248,354 B2
(45) Date of Patent: Jul. 24, 2007

(54) APPARATUS FOR INSPECTION OF A WAFER

(75) Inventors: Albert Kreh, Solms (DE); Henning Backhauss, Wetzlar (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 431 days.

(21) Appl. No.: 10/854,275

(22) Filed: May 27, 2004

(65) Prior Publication Data

US 2005/0002023 A1  Jan. 6, 2005

(30) Foreign Application Priority Data

Jul. 3, 2003  (DE) ................. 103 30 005

(51) Int. Cl.
*G01N 21/00* (2006.01)

(52) U.S. Cl. .................................. 356/237.5

(58) Field of Classification Search ... 356/237.1–239.8
See application file for complete search history.

(56) References Cited

U.S. PATENT DOCUMENTS

| | | | |
|---|---|---|---|
| 4,772,126 A | | 9/1988 | Allemand et al. |
| 4,952,058 A | * | 8/1990 | Noguchi et al. ........... 356/237.5 |
| 5,046,847 A | * | 9/1991 | Nakata et al. ............... 356/338 |
| 5,495,330 A | | 2/1996 | Champaneri et al. |
| 5,909,276 A | * | 6/1999 | Kinney et al. ............ 356/237.2 |
| 6,020,957 A | * | 2/2000 | Rosengaus et al. ....... 356/237.4 |
| 6,263,099 B1 | | 7/2001 | Maeda et al. |
| 6,288,780 B1 | * | 9/2001 | Fairley et al. ............ 356/237.1 |
| 6,292,260 B1 | | 9/2001 | Lin et al. |
| 6,512,578 B1 | | 1/2003 | Komatsu et al. |
| 6,621,570 B1 | * | 9/2003 | Danko ...................... 356/237.4 |
| 6,633,375 B1 | | 10/2003 | Veith et al. |
| 6,724,474 B1 | * | 4/2004 | Heo et al. ................. 356/237.4 |
| 6,774,991 B1 | * | 8/2004 | Danko ...................... 356/237.4 |
| 7,064,820 B2 | * | 6/2006 | Isozaki et al. ............ 356/237.2 |

FOREIGN PATENT DOCUMENTS

| | | |
|---|---|---|
| DE | 195 34 347 A1 | 4/1996 |
| DE | 199 03 486 A1 | 8/2000 |
| DE | 100 48 432 A1 | 5/2001 |
| DE | 100 28 201 A1 | 12/2001 |
| WO | WO 99/02977 A1 | 1/1999 |

OTHER PUBLICATIONS

Peterson et al., "Lithography Defects: Reducing and Managing Yield Killers Through Photo Cell Monitoring," Yield Management Solutions, (Spring 2000), pp. 17-24.

* cited by examiner

*Primary Examiner*—Gregory J. Toatley, Jr.
*Assistant Examiner*—Isiaka O. Akanbi
(74) *Attorney, Agent, or Firm*—Foley & Lardner LLP (57) ABSTRACT

The invention concerns an apparatus for inspection of a wafer, encompassing at least one incident-light illumination device that radiates an illuminating light beam which is incident obliquely onto a surface of a wafer to be inspected, and an image capture device for capturing an image of the surface in a dark-field arrangement. The wafer inspection apparatus is characterized in that at least one deflection device is provided in order to deflect an associated illuminating light beam onto the surface of the wafer.

27 Claims, 5 Drawing Sheets

APPARATUS FOR INSPECTION OF A WAFER

CROSS REFERENCE TO RELATED APPLICATIONS

This application claims priority of the German patent application 103 30 005.8 which is incorporated by reference herein.

FIELD OF THE INVENTION

The present invention concerns an apparatus for inspection of a wafer, and concerns in particular an apparatus for the detection of macrodefects on the surface of wafers.

BACKGROUND OF THE INVENTION

In semiconductor production, wafers are processed sequentially in a plurality of process steps during the production process. With increasing integration density, requirements in terms of the quality of features configured on the wafer are rising. It is advantageous for this purpose if the quality even of individual process steps, for example lithography steps, can be dependably assessed during the production process and prior to a subsequent process step. The reason is that if a determination can be made, directly after a process step is performed and before final completion of a production process, that a wafer or the features configured on a wafer are defective, the wafer can be immediately discarded with no need to perform other subsequent process steps. Or the wafer identified as defective can be given special additional treatment until satisfactory quality is achieved. Efficiency and yield in semiconductor processing can thus be improved.

Optical apparatuses are particularly suitable for inspecting the surface of wafers. Optical apparatuses are known that can detect, by image recognition, a very wide variety of features on the surface of a wafer, the wafer usually being bright-field illuminated and scanned with a camera (matrix or line camera).

An inspection apparatus of this kind of the KLA-Tencor Corporation is described in the article "Lithography Defects: Reducing and Managing Yield Killers through Photo Cell Monitoring," by Ingrid Peterson, Gay Thompson, Tony DiBiase, and Scott Ashkenaz, Spring 2000, Yield Management Solutions. The wafer inspection apparatus described therein works with an incident-light illumination device that examines microdefects with low contrast using a bright-field/dark-field illumination system.

U.S. Pat. No. 4,772,126 discloses an apparatus and a method for the detection of particles on the surface of a wafer. The wafer is held rotatably on a wafer receiving device. Two laser beams are incident, mutually orthogonally in projection onto the surface of the wafer, onto the surface of the wafer at a raking incidence angle. Scattered light that derives from defects and particles on the surface of the wafer in the illuminated region is imaged, in a dark-field arrangement, into an image capture device oriented perpendicular to the surface of the wafer, and subsequently evaluated. The laser beams are imaged onto the surface of the wafer by means of lenses that are arranged at the circumferential edge of the wafer. A certain minimum spacing between the lens and the circumferential edge of the wafer must be maintained; this considerably limits imaging capabilities.

U.S. Pat. No. 6,292,260 B1 discloses an apparatus and a method for optical inspection of surface features on a wafer. Two laser beams are incident oppositely and at a raking incidence angle onto the surface of a wafer, a projection of the illuminating light beams onto the surface of the wafer enclosing an angle of 45° with the respective linear features extending on the surface of the wafer. The laser light sources are arranged directly at the circumferential edge of the wafer, which increases the base area of the inspection apparatus and is disadvantageous in terms of performing contamination-creating maintenance work on the laser light sources.

WO 99/02977 discloses an apparatus and a method for inspection of the surface of a wafer, one or two laser beams being incident at 45°, in projection onto the surface of the wafer, with respect to the features on the wafer. Light reflected directly from the surface of the wafer, and diffraction orders that derive from diffraction of the incident light at the features on the surface of the wafer, are detected in spectrally resolved fashion in a bright-field arrangement using an image capture device, and evaluated.

With the aforementioned inspection apparatuses, the variation capabilities in terms of imaging the illuminating light beams onto the surface of the wafer are limited. It is additionally disadvantageous that the adjustment of light sources and imaging optical elements that are arranged in the vicinity of the circumferential edge of the wafer is difficult, and can result in damage to the wafer surface.

SUMMARY OF THE INVENTION

It is the object of the present invention to create an apparatus for inspection of a wafer in which the variation capabilities for imaging of the illuminating light beams are greater, and in which easier alignment of the illuminating light beams can be achieved.

This object is achieved by an apparatus for inspection of a wafer, comprising: at least one incident-light illumination device that radiates an illuminating light beam which is incident obliquely onto a surface of the wafer to be inspected, at least one deflection device in order to deflect the illuminating light beam onto the surface of the wafer; and an image capture device for capturing an image of the surface in a dark-field arrangement.

The above object is achieved as well by an apparatus for inspection of a wafer, comprising: at least one incident-light illumination device that radiates an illuminating light beam which is incident obliquely onto a surface of the wafer to be inspected, at least one deflection device in order to deflect the illuminating light beam onto the surface of the wafer; an image capture device for capturing an image of the surface in a dark-field arrangement; and a separation panel having at least one deflection device arranged below the separation panel and adjacent to the wafer and the at least one incident-light illumination device and the image capture device arranged above the separation panel.

According to the present invention, the wafer inspection apparatus encompasses an incident-light illumination device that radiates an illuminating light beam which is incident obliquely onto a surface of a wafer to be inspected, as well as an image capture device for capturing an image of the surface in a dark-field arrangement. The apparatus is characterized in that at least one deflection device is provided in order to deflect an associated illuminating light beam onto the surface of the wafer to be inspected.

The deflection of the at least one illuminating light beam in a different direction makes available, in the context of the apparatus according to the present invention, an additional degree of freedom that advantageously increases the variation capabilities for designing wafer inspection apparatuses, and makes possible easier alignment. Because of the deflection of the at least one illuminating light beam in a different direction, comparatively bulky imaging optical systems, for example lenses or objectives, which are used for imaging of the illuminating light beams onto the surface of the wafer and beam shaping, do not necessarily need to be arranged in the immediate vicinity of the circumferential edge of the wafer; they can instead be arranged at a greater distance from the wafer and at a different suitable location in the wafer inspection apparatus. The incident-light illumination devices themselves can be even more variably arranged in the wafer inspection apparatus, for example substantially vertically above the wafer, so that the base area of the wafer inspection apparatus can be reduced even further. In addition, the incident-light illumination devices can also be even more variably oriented, for example can be aligned perpendicular to the surface of the wafer. For alignment of the wafer inspection apparatus, it may be sufficient to align only the deflection device and not also other elements, for example the imaging optics or the incident-light illumination device.

The illuminating light beam radiated by the at least one incident-light illumination system is incident obliquely onto the surface of the wafer to be inspected, and is thus reflected at a non-infinitesimal return angle relative to a normal line onto the surface of the wafer. The image capture device is arranged in a dark-field arrangement, so that the illuminating light reflected from the surface of the wafer is preferably completely blocked out of the image capture device, and the latter instead captures only scattered or diffracted light deriving from an illuminated region on the surface of the wafer. The captured image is preferably read out digitally and further processed. The incident-light illumination device can illuminate the entire surface of the wafer or definable portions on the surface of the wafer, for example portions encompassing dies or several dies. The image field of the image capture device preferably corresponds to the illuminated surface region.

The deflection device preferably images the associated illuminating light beam directly, i.e. without the use of downstream imaging optics, onto the surface of the wafer. For example, the deflection device can be a mirror that reflects a divergent illuminating light beam directly onto the surface of the wafer. Or the deflection device can be a convexly or concavely curved mirror that, in addition to deflecting the illuminating light beam, also provides for suitable spreading or focusing thereof. Or the deflection device can be a diffractive optical element, for example a diffraction grating, that suitably shapes and images the illuminating light beam. Or the deflection device can be a refractive optical element, for example a prism or prism arrangement, that suitably shapes and images the illuminating light beam.

Because the base area of mirrors, curved mirrors, diffractive optics, refractive optics, or comparable deflection devices is comparatively small, the deflection devices can be arranged directly at the circumferential edge of the wafer, or above it, or even at a short distance from the surface of the wafer; this advantageously increases variation capabilities for imaging of the illuminating light beams.

According to a very particularly preferred embodiment, the deflection device encompasses in each case a mirror that reflects the illuminating light beam onto the surface of the wafer. The mirror is preferably a plane mirror. In this arrangement, the incident-light illumination device can be arranged above or next to the wafer as seen in a plan view onto the wafer inspection apparatus. The incident-light illumination device can, in principle, have any orientation. It is very particularly preferred, however, if the incident-light illumination device is oriented substantially perpendicular or parallel to the surface of the wafer.

According to a further particularly preferred embodiment, the at least one deflection device encompasses in each case a periscope arrangement of mirrors that folds the beam path of the associated illuminating light beam. The mirrors of the periscope arrangement are preferably arranged parallel to one another but offset in elevation, in very particularly preferable fashion vertically above one another, so that the illuminating light beam is deflected from a first, higher elevation to a second, lower elevation.

The mirror or mirrors of the deflection device are preferably held pivotably and/or displaceably, so that the incidence angle at which the illuminating light beam is incident onto the surface of the wafer can be varied. The deflection device is preferably designed in such a way that neither the wafer nor the incident-light illumination device needs to be moved in order to modify the incidence angle.

Because the illuminating light beam is offset in elevation, as mentioned above, in the context of imaging onto the surface of the wafer, the incident-light illumination device, imaging optics, and further optical elements (e.g. filters, beam splitter mirrors, etc.) can be arranged so that there is less impediment to a flow of clean-room air through the wafer inspection apparatus. It is known that wafer inspection apparatuses are used in clean rooms, where a continuous air circulation must be maintained so that no troublesome particles can settle onto the surface of a wafer. It is thus important to ensure that the flow of clean-room air be impeded as little as possible. The flow of clean-room air through the wafer inspection apparatus is impeded in particular by the comparatively large incident-light illumination devices, for example laser light sources, flash lamps, fiber optics, etc., and by the bulky imaging optics themselves. According to the present invention, these elements that impede the circulation of clean-room air can be arranged at locations within or even outside the wafer inspection apparatus where they present the least interference.

According to a preferred embodiment, the wafer inspection apparatus is spatially divided by means of a substantially horizontally oriented separation panel. The separation panel has at least one opening so that the incident illuminating light beam, and/or light from the surface of the wafer, can pass vertically through the separation panel. The wafer inspection apparatus is preferably designed so that the wafer can be arranged below the separation panel, and so that the at least one incident-light illumination device and/or the image capture device, as well as the most important optical elements for imaging the associated illuminating light beam onto the surface of the wafer, are arranged above the separation panel. The wafer is thus protected in the event of maintenance and installation work above the separation panel. The spatial subdivision reduces the costs of the wafer inspection apparatus and simplifies procedures related to the maintenance, operation, and repair of the wafer inspection apparatus.

The wafer is preferably mounted movably below the separation panel. A movable stage having an associated wafer receiving device can be provided below the separation panel for this purpose. The separation panel protects the elements arranged above it, for example the incident-light illumination devices and the image capture device and imaging optical elements, from mechanical damage caused by the movable stage. Conversely, maintenance and installation work can be performed on elements arranged above the separation panel without creating a risk of injury due to rapid movement of the movable stage or the wafer.

The openings in the separation panel can be closed off in airtight fashion by a transparent element, for example a transparent disk. The transparent element provided in the at least one opening can also be used as a homogenizing means for homogenization of the illuminating light beam, e.g. can be present in the form of a diffusion disk, or can serve for further imaging and shaping of the illuminating light beam, e.g. in the form of a lens. For homogenization of the illuminating light beam, the surface of a mirror serving as deflection device can also be roughened or mechanically machined in appropriate fashion.

The imaging axis defined by the image capture device is preferably oriented perpendicular to the surface of the wafer to be inspected, so that the dark-field arrangement is implemented by oblique incidence of the illuminating light onto the surface. In principle, however, the imaging axis can also be inclined with respect to the surface of the wafer, provided the illumination angle is not equal to the imaging angle, since otherwise the dark-field arrangement could no longer be implemented. The image capture device is preferably stationary relative to the surface of the wafer.

The illumination axis established by the incident-light illumination device, and the imaging axis established by the image capture device, preferably span a plane that is oriented perpendicular to the surface of the wafer. In this arrangement, the incident-light illumination device and the image capture device can be aligned in advantageously simple fashion. In principle, the aforesaid plane can also intersect the surface of the wafer at a different angle, up to a relative angle of only a few degrees.

To make the design of the apparatus even more flexible, the incidence angle $\alpha$ of the illuminating light beam can also be modified, a region on the surface of the wafer illuminated by the incident illuminating light beam preferably remaining stationary upon modification of the incidence angle so that, advantageously, the orientation of the image capture device does not need to be modified. Modification of the incidence angle $\alpha$ thus allows defects on the surface of the wafer to be identified and evaluated under different illumination conditions.

In order to modify the incidence angle $\alpha$, the incident-light illumination device can comprise an alpha-angle adjustment mechanism, for example a curved alignment rail along which the incident-light illumination device can be displaced, the radius of the alignment rail being coordinated with the distance between the incident-light illumination device and the incidence point of the illumination axis on the surface of the wafer in such a way that the illuminated region on the surface of the wafer remains stationary upon modification of the incidence angle.

The incidence angle can be varied over a wide range in the apparatus according to the present invention, for example in the range between approximately 3° and approximately 90°, preferably in the range from approximately 20° to approximately 90°. Incidence angles in the range from approximately 40° to approximately 86° are particularly preferred according to the present invention. It should be noted, however, that a raking incidence of the illuminating light onto the surface of the wafer is also theoretically a possibility.

The at least one incident-light illumination device can be a monochromatic light source, for example an LED or a linear LED arrangement, in which case a black-and-white image capture device can also be used. Preferably, however, the incident-light illumination device is a polychromatic light source, for example a flash light source or a linear flash light source arrangement, in which case the scattered light captured by the image capture device is detected and analyzed in spectrally resolved fashion. The spectral scattered light distribution also allows further information to be obtained regarding the causes of defects.

According to a further embodiment, the wafer inspection apparatus furthermore encompasses a wafer receiving device to which the wafer to be inspected can be transferred in aligned fashion. For alignment of the wafer, the wafer inspection apparatus can have associated with it a prealigner which determines the location of a notch or flat on the outer circumference of the wafer, aligns the wafer on the basis of the notch or flat, and then transfers it to the wafer receiving device while retaining the defined orientation. If the layout of the features to be configured on the wafer is known, the orientation of the illumination axis defined by the respective illuminating light beam can then be coordinated in such a way that its projection onto the surface of the wafer is aligned at a definable orientation with respect to the features on the surface of the wafer. Those features can extend in substantially linear fashion on the surface of the wafer to be inspected.

An image capture device that encompasses an objective and a linear or matrix camera is preferably used for the inspection of macrodefects. For automatic inspection of the surface of the wafer, the apparatus according to the present invention is connected to a data readout device, for example a computer or frame grabber, which sequentially reads out the image data of the linear or matrix camera. Parameters or defects of the wafer can then be determined from the image data that are read out. In particular, the evaluation of defects on the surface of the wafer can also be performed in spatially resolved fashion, for which purpose the data from the data readout device are coordinated, for example, with respect to markings on the surface or at the edge of the wafer.

BRIEF DESCRIPTION OF THE DRAWINGS

The invention will be described below by way of example with reference to the appended Figures, from which further features, advantages, and objects to be achieved may be inferred. In the Figures.

In the Figures, identical reference characters designate identical or identically functioning elements or assemblies.

DETAILED DESCRIPTION OF THE INVENTION

Figure 1:
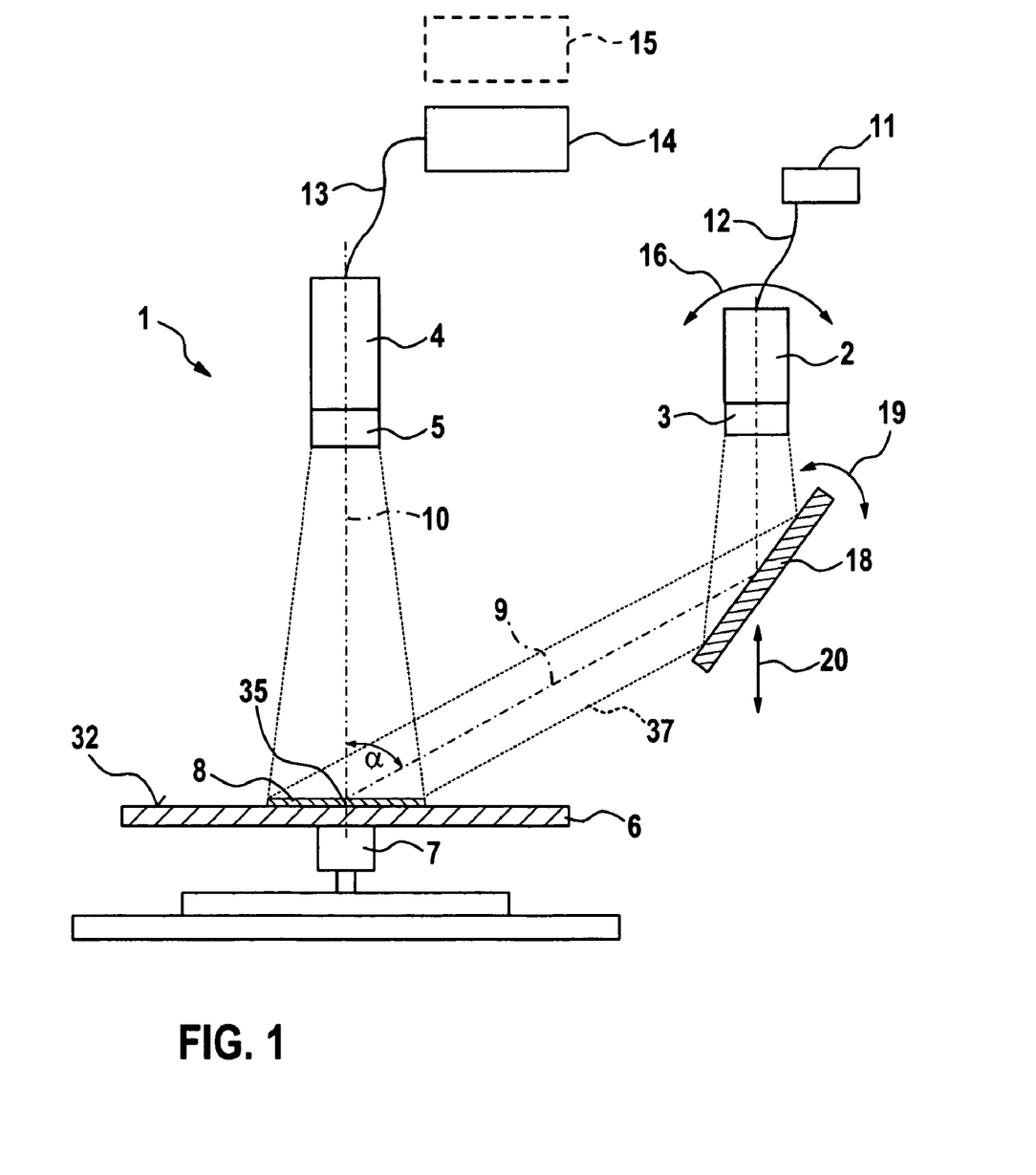
FIG. 1 is a cross section through a first embodiment of a wafer inspection apparatus according to the present invention.

FIG. 1 shows, in a schematic cross section, a wafer inspection apparatus 1 according to the present invention. It encompasses an incident-light illumination device 2 that defines an illumination axis 9 which intersects surface 32 of wafer 6 at incidence point 35, a camera 4 serving as image capture device, and a wafer receiving device 7 that holds wafer 6 in either stationary or rotatable fashion. Wafer 6 is vacuum-suctioned onto wafer receiving device 7. Incident-light illumination device 2 comprises an imaging optical element 3 that shapes illuminating light beam 37 in such a way that illuminating light beam 37, incident in inclined fashion onto surface 32 of wafer 6 to be inspected, illuminates a corresponding region 8 that covers the entire surface of wafer 6 or a subregion thereof, for example individual dies.

Camera 4 is perpendicular to surface 32 of wafer 6 and defines an imaging axis 10 that intersects surface 32 of wafer 6 at incidence point 35. An objective 5 is arranged at the front end of camera 4 so that illuminated region 8 is imaged into camera 4. Imaging axis 10 and illumination axis 9 span a plane that is orthonormal to surface 32 of wafer 6. In principle, this plane can also intersect surface 32 of wafer 6 at a different angle.

In FIG. 1, camera 4 and incident-light illumination device 2 are arranged in a dark-field arrangement, so that what is imaged into camera 4 is not illuminating light reflected directly from surface 32 of wafer 6, but only scattered light deriving from defects on surface 32 of wafer 6 in illuminated region 8. As FIG. 1 shows, illumination axis 9 is inclined with respect to surface 32 of wafer 6. Illumination axis 9 encloses with imaging axis 10 an incidence angle $\alpha$ that corresponds, in the example depicted, to a normal line onto surface 32 of wafer 6. Incidence angle $\alpha$ is selected as appropriate; this can also be dependent on the features to be configured on wafer 6. Although incidence angle $\alpha$ can in principle be varied over a wide range, e.g. from 3° to approximately 90° and more preferably from approximately 20° to approximately 90°, it is preferred if the illuminating light beam strikes surface 32 of wafer 6 at an incidence angle $\alpha$ in the range from approximately 40° to approximately 86°.

As shown in FIG. 1, illuminating light beam 37 is deflected in a different spatial direction by means of a deflection mirror 18 serving as deflection device. Illuminating light beam 37 reflected from the surface of deflection mirror 18 is imaged directly onto surface 32 of wafer 6. As indicated by double arrows 19 and 20, deflection mirror 18 can be pivoted and moved in elevation. In combination with the pivoting capability of incident-light illumination device 2 indicated by double arrow 16, incidence angle $\alpha$ can thus be modified over a wide range.

As is also evident from FIG. 1, deflection mirror 18 can also be arranged in the immediate vicinity of the circumferential edge of wafer 6, so that a raking incidence of illuminating light beam 37 can also be easily implemented. According to the present invention, any imaging optics that serve to image and shape the illuminating light beam, such as a lens or an objective, can be arranged upstream from deflection mirror 18.

According to FIG. 1, incident-light illumination device 2 is oriented perpendicular to surface 32 of wafer 6, and incident-light illumination device 2 is located, in a plan view of wafer inspection apparatus 1, alongside surface 32 of wafer 6. Because of the deflection, the position and orientation of incident-light illumination device 2 can still be very variable. For example, incident-light illumination device 2 can also be oriented substantially parallel to the surface of the wafer and can be arranged, in a plan view of wafer 6, alongside wafer 6; and illuminating light beam 37 that is reflected by deflection mirror 18 can be incident onto surface 32 of wafer 6 in substantially radially inwardly directed fashion.

By appropriate coordinated pivoting of incident-light illumination device 2 and deflection mirror 18, and by vertical and/or horizontal displacement of deflection mirror 18, it is possible to ensure that as incidence angle $\alpha$ is modified, the location of illuminated region 8 on surface 32 of wafer 6 remains substantially stationary.

While FIG. 1 shows that deflection mirror 18 is a plane mirror, the latter can also be replaced by a convex or concave mirror; by diffractive optical elements, for example diffraction gratings; or by refractive optical elements, for example prisms or prism arrangements.

A light source can be provided directly in incident-light illumination device 2. As depicted in FIG. 1, incident-light illumination device 2 can also encompass an external light source 11 whose light is coupled into the beam path via a light guide bundle 12. Light source 11 can be a monochromatic or polychromatic light source.

LEDs or linear LED arrangements are especially suitable as monochromatic light sources. Flash lamps, white light LEDs, halogen lamps, fluorescent tubes, and the like are especially suitable as polychromatic light sources. Light source 11 can be operated continuously. Preferably, however, light source 11 is operated in timed fashion, for example as flash light that is triggered synchronously with image capture, i.e. whenever a new wafer 6 is transferred in oriented fashion to wafer receiving device 7.

In very particularly preferred fashion, linear fiber illuminators, whose light is radiated in linear fashion and shaped with a cylindrical lens in order to illuminate region 8 homogeneously, are used as incident-light illumination device 2.

Camera 4 is connected via a data line 13 to a data readout device 14 that evaluates the captured image data or temporarily stores them, e.g. for later image evaluation. Data readout device 14 is preferably a computer having a frame grabber that reads out the lines of a CCD camera 4 periodically or in timed fashion, for example synchronously with the triggering of the flash light. The image data that are read out can also be displayed on monitor 15, or displayed there after evaluation by means of suitable software.

Figure 2:
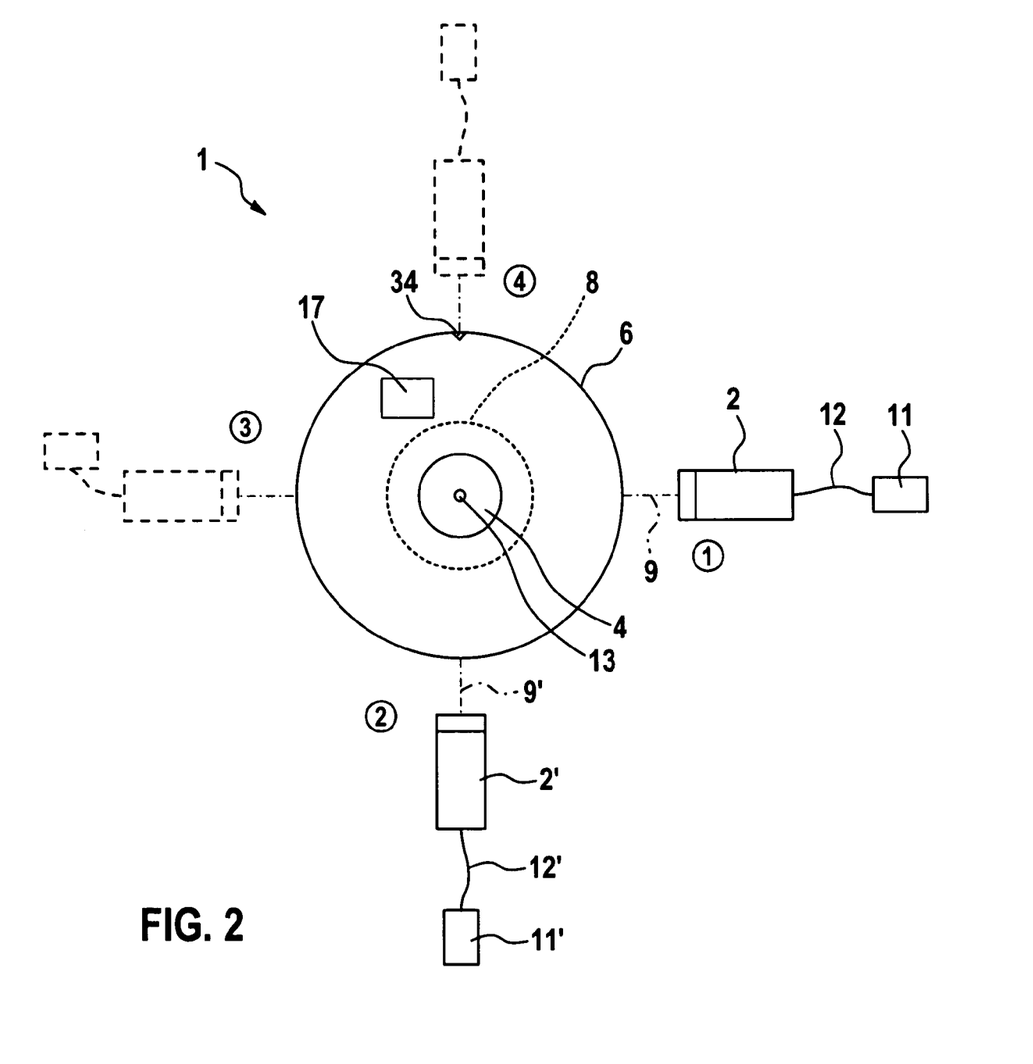
FIG. 2 is a plan view of the apparatus according to FIG. 1.

FIG. 2 shows wafer inspection apparatus 1 according to FIG. 1 in a schematic plan view. As depicted in FIG. 2, wafer inspection apparatus 1 encompasses two incident-light illumination devices 2, 2' that, as seen in a plan view of wafer 6, are oriented at right angles to one another. The light of light source 11, 11' is coupled via respective light guide bundles 12, 12' into the respective incident-light illumination devices 2, 2'. As depicted in FIG. 2, wafer 6 is held in a definable orientation in wafer inspection apparatus 1.

Linearly extending features (not depicted) that can subdivide the surface of wafer 6 into rectangular subregions 17, for example into individual dice, can be configured on the surface of wafer 2. A notch 34 or a flat, which serves for orientation of wafer 6, is provided on the circumferential edge of wafer 6. All the process steps for configuring features on wafer 6 are performed with wafer 6a in a defined orientation. Because the layout of the structures to be configured is known, the manner in which the linear features extend can be inferred unequivocally from the location of the flat or notch 34 on the circumferential edge of wafer 6. Wafer 6 can in turn be oriented in predefinable fashion by means of a prealigner. The prealigner (not depicted) can be a component of wafer inspection apparatus 1 or can be positioned upstream from wafer inspection apparatus 1, in which case wafer 6 is transferred to wafer inspection apparatus 1 with a definable orientation.

As indicated by the dashed lines in FIG. 2, several possibilities exist for arranging two incident-light illumination devices 2 around wafer 6 in such a way that the projections of the respective illumination axes onto the surface of wafer 6 are substantially orthogonal to one another. These positions are the positions labeled in FIG. 2 with numbers 1 through 4. Incident-light illumination devices 2, 2' arranged at the positions labeled with numbers 1 through 4 can be activated selectively. According to the present invention, the two illuminating light beams can be incident mutually orthogonally or oppositely to one another, in projection onto the surface of wafer 6, if only two incident-light illumination devices 2 are used. It is important to ensure that region 8 illuminated by one respective incident-light illumination device 2 sufficiently, preferably substantially completely, overlaps region 8 illuminated by a different incident-light illumination device 2'.

In very particularly preferred fashion, the geometry used is one with two incident-light illumination devices 2, 2' that radiate onto the surface of wafer 6 in such a way that the projections of illumination axes 9, 9' onto surface 32 of wafer 6 extend mutually orthogonally and intersect at an incidence point where imaging axis 10 of camera 4 also intersects the surface of wafer 6.

Figure 3:
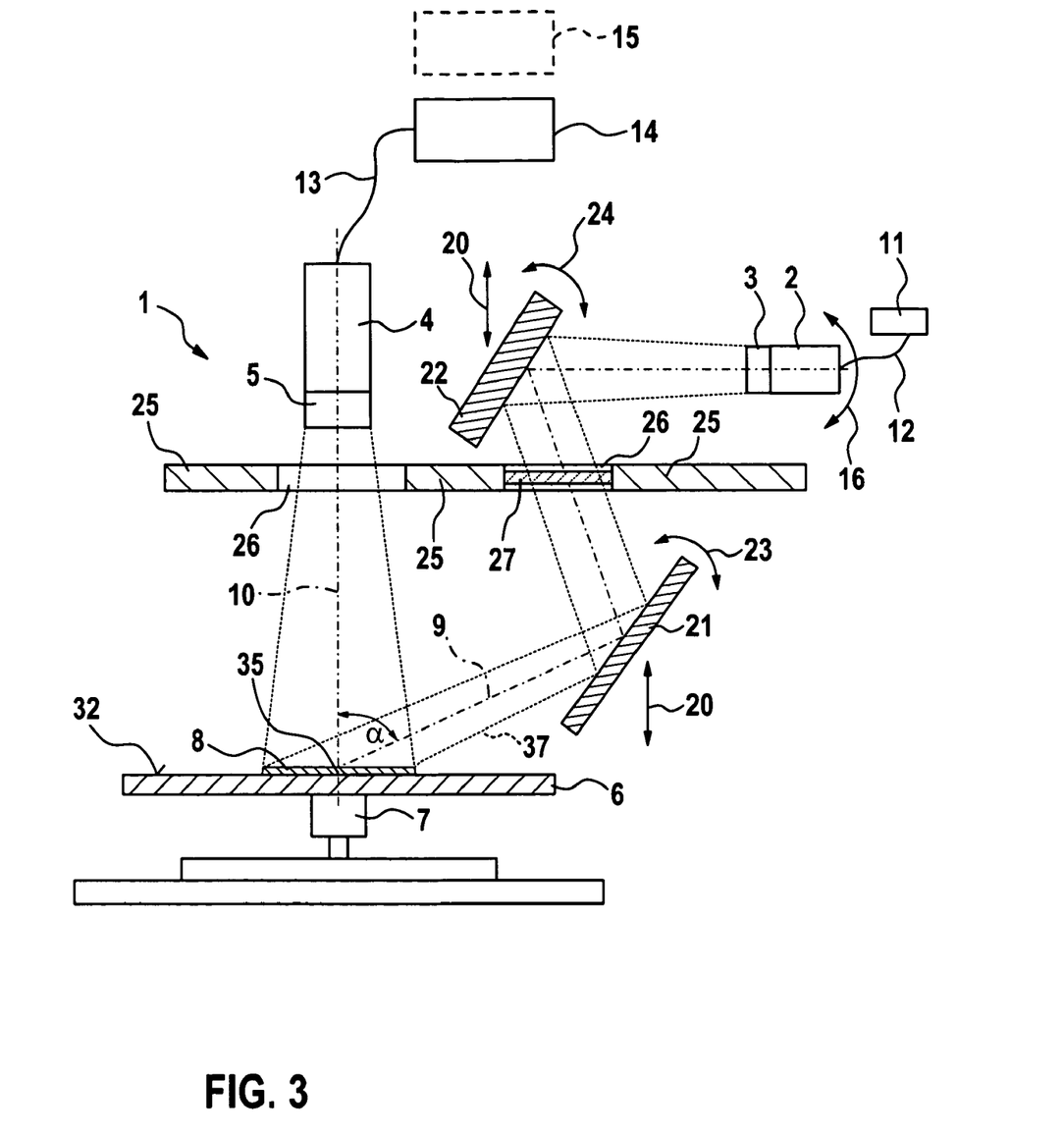
FIG. 3 is a cross section through a further embodiment of a wafer inspection apparatus according to the present invention.

FIG. 3 shows a cross section through a further embodiment of a wafer inspection apparatus according to the present invention. According to FIG. 3, deflection mirror 18 is replaced by a periscope arrangement of deflection mirrors 21, 22 which fold the beam path of illuminating light beam 37 and offset it in elevation. The two deflection mirrors 21, 22 are arranged substantially parallel to, but with an elevation offset from, one another. As indicated by double arrows 20, the two deflection mirrors 21, 22 can be moved, separately or together in coordinated fashion, in elevation and/or perpendicular to that direction. As indicated by double arrows 23, 24, the two deflection mirrors 21, 22 can be pivoted separately or in coordination with one another. As indicated by double arrow 16, the incident-light illumination device can also be pivoted. Incidence angle α at which the illuminating light beam is incident onto surface 32 of wafer 6 can thus be modified, the location of illuminated region 8 on surface 32 of wafer 6 remaining substantially unchanged upon modification of incidence angle α. With the periscope arrangement, the spreading of the illuminating light beam can also be easily modified.

A periscope arrangement in which lower deflection mirror 21 is held stationary and only upper deflection mirror 22 can be pivoted and/or displaced vertically is preferred. In this configuration, alignment of illuminating light beam 37 can be performed only by means of upper deflection mirror 22.

Other optical elements, for example curved mirrors, diffractive elements such as diffraction gratings, or even prisms or prism arrangements, are of course also suitable for deflecting illuminating light beam 37 in the periscope arrangement.

According to FIG. 3, a separation panel 25 effects a spatial subdivision of wafer inspection apparatus 1. In the example depicted, wafer 6 and lower deflection mirror 21 of the periscope arrangement of deflection mirrors 21, 22 are arranged below separation panel 25; and the at least one incident-light illumination device 2, image capture device 4, upper deflection mirror 22 of the periscope arrangement of deflection mirrors 21, 22, as well as further optical elements (not depicted), are arranged above separation panel 25. Separation panel 25 provides a certain mechanical protection for elements located below separation panel 25, for example wafer 6 or lower mirror 21. Because most elements are arranged above separation panel 25—in particular image capture device 4, incident-light illumination device 2, and upper mirror 22—maintenance and installation work can be performed on these elements with no risk of damage to wafer 6 or to lower mirror 21, and with no risk of injury because of a movable stage (not depicted) arranged below separation panel 25.

Separation panel 25 comprises several openings 26 through which pass the imaging light beam imaged into image capture device 4, as well as illuminating light beam 37. Right-hand opening 26 is closed off, preferably in airtight fashion, by a transparent element 27. Left-hand opening 26 is open in the exemplary embodiment depicted, but can likewise be closed off by a transparent element.

Separation panel 25 can, of course, also be omitted in the context of the periscope arrangement of deflection mirrors 21, 22 as shown in FIG. 3.

Figure 4:
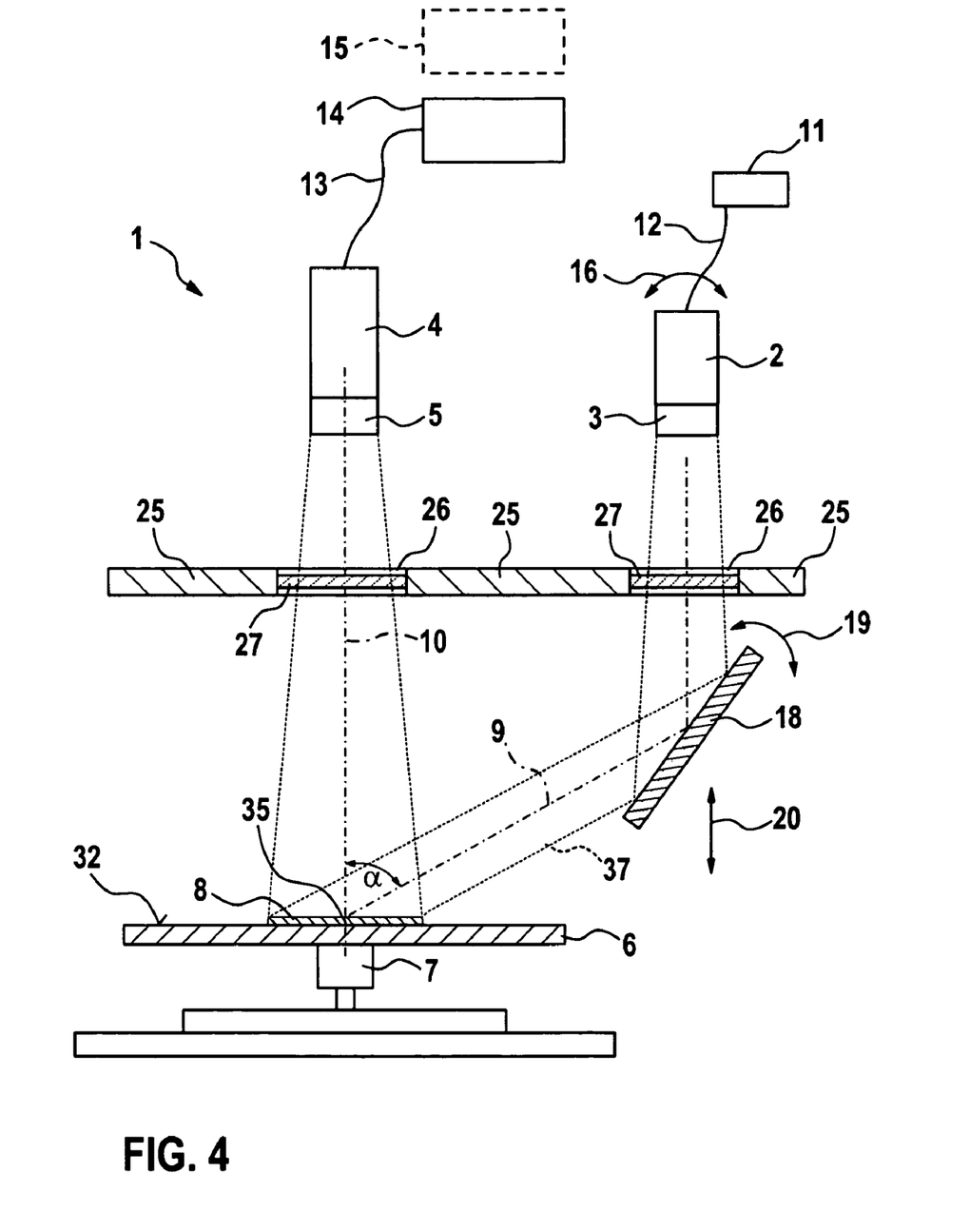
FIG. 4 is a cross section through a further embodiment of a wafer inspection apparatus according to the present invention.

FIG. 4 shows, in a schematic cross section, a further embodiment of a wafer inspection apparatus 1 according to the present invention. The arrangement is substantially identical to that shown in FIG. 1, with the exception of separation panel 25 that spatially subdivides wafer inspection apparatus 1 into two levels offset from one another in elevation. As depicted, a transparent disk 27 is located respectively in left-hand and in right-hand opening 26 of separation panel 25. This transparent disk can encompass a homogenization means, for example a diffusion disk or microlens array, serving to homogenize the respective light beam.

Figure 5:
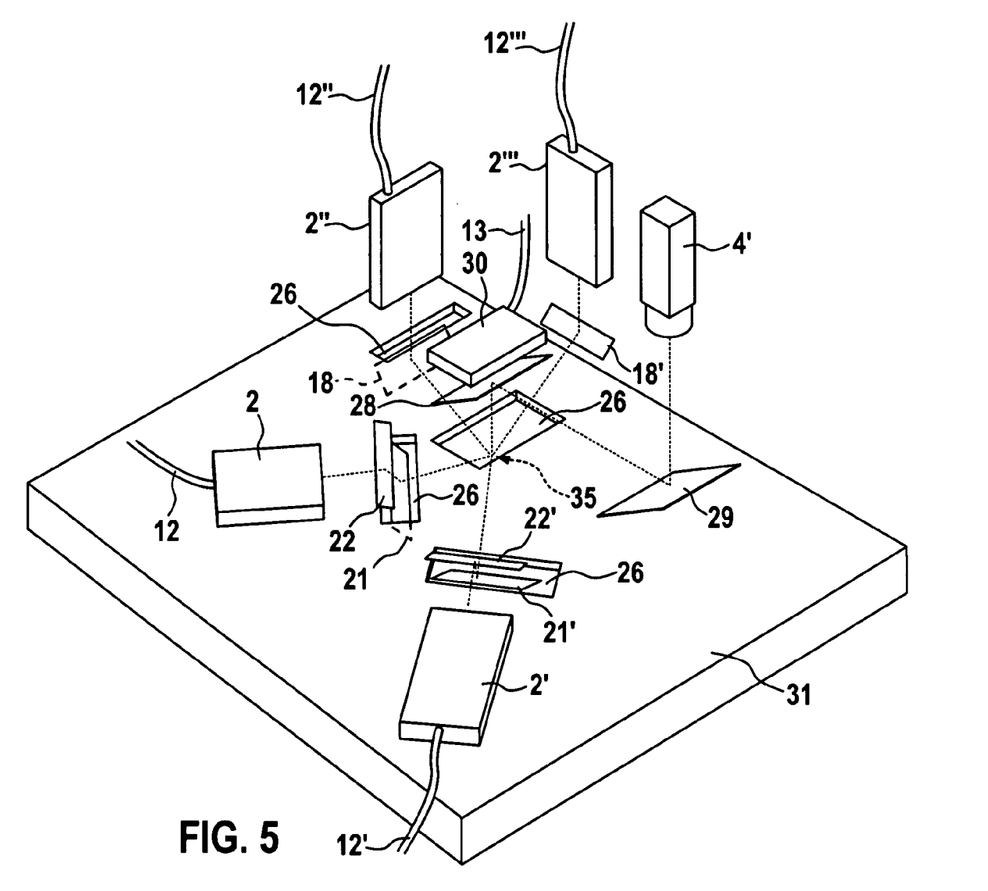
FIG. 5 is a schematic perspective view of a further embodiment of a wafer inspection apparatus according to the present invention.

FIG. 5 shows, in a perspective arrangement, a further embodiment of a wafer inspection apparatus 1 according to the present invention. All the elements are placed on a mounting plate 31. In the lower part, incident-light illumination devices 2, 2' are oriented parallel to the surface of the wafer (not depicted). The respective illuminating light beams 37 are imaged onto the surface of the wafer at an inclined incidence angle via the associated periscope arrangements of deflection mirrors 22, 21 and 22', 21'. Camera 4 serves to capture scattered light that derives from the illuminated region on the surface of the wafer. Camera 4 is oriented perpendicular to the surface of the wafer. The light scattered in the illuminated region on the surface of the wafer is imaged via semitransparent mirror 28 and deflection mirror 29 into camera 4. Located above semitransparent mirror 28 is a large-area illuminator 30 that can be used for other inspection methods.

Located in the upper part are two further incident-light illumination devices 2", 2'" whose illuminating light beams are imaged by means of associated deflection mirrors 18, 18' onto the surface of the wafer (not depicted) in the manner described in conjunction with FIG. 1. In projection onto the surface of the wafer, both the illuminating light beams radiated from incident-light illumination devices 2, 2', and the illuminating light beams radiated from incident-light illumination devices 2" and 2'", extend perpendicular to one another.

Although not depicted in the Figures described above, wafer inspection apparatus 1 according to the present invention encompasses a movable stage, for example an X-Y displacement stage, so that the entire surface 32 of wafer 6 can be scanned by suitable displacement of wafer 6.

What is claimed is:

1. An apparatus for inspection of a wafer, comprising:
   at least one incident-light illumination device arranged above a separation panel, wherein the separation panel is positioned between the wafer and the incident-light illumination device, wherein the at least one incident-light illumination device radiates an illuminating light beam through at least one opening in the separation panel onto a surface of the wafer to be inspected, at least one deflection device that is arranged below the separation panel in order to deflect the illuminating light beam onto the surface of the wafer, wherein the illuminating light beam is incident obliquely to the surface of the wafer; and an image capture device to capture an image of the surface in a dark-field arrangement, wherein the image capture device is arranged above the separation panel.

2. The apparatus as defined in claim 1, wherein the at least one deflection device comprises a mirror.

3. The apparatus as defined in claim 1, wherein the at least one incident-light illumination device is oriented perpendicular to the surface of the wafer.

4. The apparatus as defined in claim 1, wherein the at least one incident-light illumination device is oriented parallel to the surface of the wafer.

5. The apparatus as defined in claim 1, in which the at least one deflection device comprises a periscope arrangement of mirrors, wherein the at least one incident-light illumination device is oriented parallel to the surface of the wafer.

6. The apparatus as defined in claim 5, wherein at least one mirror held pivotably and/or displaceably.

7. The apparatus as defined in claim 1, wherein the image capture device defines an imaging axis oriented perpendicular to the surface of the wafer.

8. The apparatus as defined in claim 7, wherein the imaging axis and an illumination axis established by an incident-light illumination device span a plane that is oriented perpendicular to the surface of the wafer.

9. The apparatus as defined in claim 8, wherein an incidence angle of the illuminating light beam is modifiable, wherein an illuminated region on the surface of the wafer remains stationary when the incidence angle is modified.

10. The apparatus as defined in claim 9, wherein the incidence angle lies in the range from approximately 30 to approximately 90°.

11. The apparatus as defined in claim 9, wherein the incidence angle lies in the range from approximately 20° to approximately 90°.

12. The apparatus as defined in claim 9, wherein the incidence angle lies in the range from approximately 40° to approximately 86°.

13. The apparatus as defined in claim 1, wherein two incident-light illumination devices are provided whose illumination axes are oriented parallel to one another, such that regions on the surface of the wafer that are respectively illuminated by the incident-light illumination devices overlap one another.

14. The apparatus as defined in claim 1, wherein two incident-light illumination devices are provided whose illumination axes are oriented perpendicular to one another, such that regions on the surface of the wafer that are respectively illuminated by the incident-light illumination devices overlap one another.

15. The apparatus as defined in claim 1, wherein four incident-light illumination devices are provided whose illumination axes intersect in a region on the surface of the wafer that is imaged into the image capture device, wherein a first pair of the four incident-light illumination devices are arranged so that illumination axes of the first pair are orthogonal to illumination axes of a second pair of the four incident-light illumination devices.

16. The apparatus as defined in claim 1, wherein at least one incident-light illumination device comprises a monochromatic light source.

17. The apparatus as defined in claim 1, wherein at least one incident-light illumination device comprises a polychromatic light source.

18. The apparatus as defined in claim 17, wherein the polychromatic light source is a flash light source or a linear flash light source arrangement.

19. The apparatus as defined in claim 1, wherein an incident-light illumination device comprises a light guide bundle and an associated imaging optical element.

20. The apparatus as defined in claim 1, further comprising a homogenization means for homogenizing the illuminating light beam.

21. An apparatus for inspection of a wafer, comprising:
at least one incident-light illumination device;
an image capture device to capture an image of a surface of the wafer in a dark-field arrangement,
a separation panel arranged between the wafer and the at least one incident-light illumination device and between the wafer and image capture device, wherein at least one opening is formed in the separation panel,
at least one deflection device that is arranged with respect to the opening in order to deflect illuminating light beam onto the surface of the wafer.

22. The apparatus as defined in claim 21, wherein the at least one deflection device is held pivotably and/or displaceably.

23. The apparatus as defined in claim 22, wherein the image capture device defines an imaging axis oriented perpendicular to the surface of the wafer.

24. The apparatus as defined in claim 21, wherein an incidence angle of the illuminating light beam is modifiable and lies in the range from approximately 40° to approximately 86°.

25. The apparatus as defined in claim 21, wherein the at least one deflection device comprises a periscope arrangement of mirrors.

26. The apparatus as defined in claim 21, wherein the at least one deflection device is arranged below the separation panel.

27. The apparatus as defined in claim 1, wherein the separation panel comprises at least two openings.

* * * * *